(12) United States Patent
Parikh et al.

(10) Patent No.: US 10,080,801 B2
(45) Date of Patent: Sep. 25, 2018

(54) FORMULATIONS OF (S)-3-(4-((4-(MORPHOLINOMETHYL)BENZYL)OXY)-1-OXOISOINDOLIN-2-YL)PIPERIDINE-2,6-DIONE

(71) Applicant: Celgene Corporation, Summit, NJ (US)

(72) Inventors: Darshan Parikh, Bridgewater, NJ (US); Anil Menon, Martinsville, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/508,719

(22) Filed: Oct. 7, 2014

(65) Prior Publication Data

US 2015/0099745 A1    Apr. 9, 2015

Related U.S. Application Data

(60) Provisional application No. 61/888,419, filed on Oct. 8, 2013.

(51) Int. Cl.
| | | |
|---|---|---|
| *A61K 47/26* | (2006.01) | |
| *A61K 31/5377* | (2006.01) | |
| *A61K 9/48* | (2006.01) | |

(52) U.S. Cl.
CPC .......... *A61K 47/26* (2013.01); *A61K 9/4858* (2013.01); *A61K 9/4866* (2013.01); *A61K 31/5377* (2013.01); *Y02A 50/414* (2018.01)

(58) Field of Classification Search
None
See application file for complete search history.

(56) References Cited

U.S. PATENT DOCUMENTS

| | | | |
|---|---|---|---|
| 2006/0154880 A1 | 7/2006 | Hensel | |
| 2011/0196150 A1* | 8/2011 | Man et al. | 540/544 |

OTHER PUBLICATIONS

Cunha, Effect of Stearic Acid on Enalapril Stability and Dissolution from Multiparticulate Solid Dosage Forms, AAPS PharmSciTech, 14 (3), Sep. 2013, pp. 1150-1157.*

* cited by examiner

*Primary Examiner* — Kathrien A Cruz
*Assistant Examiner* — Andrew P Lee
(74) *Attorney, Agent, or Firm* — Jones Day

(57) ABSTRACT

Pharmaceutical compositions and single unit dosage forms of (S)-3-(4-((4-(morpholinomethyl)benzyl)oxy)-1-oxoisoindolin-2-yl)piperidine-2,6-dione, or a pharmaceutically acceptable stereoisomer, prodrug, salt, solvate, hydrate, or clathrate, are provided herein. Also provided are methods of treating, managing, or preventing various disorders, such as cancer, an inflammatory disease and/or an immune-related disorder.

35 Claims, No Drawings

FORMULATIONS OF (S)-3-(4-((4-(MORPHOLINOMETHYL)BENZYL)OXY)-1-OXOISOINDOLIN-2-YL)PIPERIDINE-2,6-DIONE

This application claims priority to U.S. Provisional Application No. 61/888,419, filed Oct. 8, 2013, the entirety of which is incorporated herein by reference.

1. FIELD

Provided herein are formulations and dosage forms of (S)-3-(4-((4-(morpholinomethyl)benzyl)oxy)-1-oxoisoindolin-2-yl)piperidine-2,6-dione or CC-220. Methods of using the formulations and dosage forms are also provided herein.

2. BACKGROUND

Drug substances are usually administered as part of a formulation in combination with one or more other agents that serve varied and specialized pharmaceutical functions. Dosage forms of various types may be made through selective use of pharmaceutical excipients. As pharmaceutical excipients have various functions and contribute to the pharmaceutical formulations in many different ways, e.g., solubilization, dilution, thickening, stabilization, preservation, coloring, flavoring, etc. The properties that are commonly considered when formulating an active drug substance include bioavailability, ease of manufacture, ease of administration, and stability of the dosage form. Due to the varying properties of the active drug substance to be formulated, dosage forms typically require pharmaceutical excipients that are uniquely tailored to the active drug substance in order to achieve advantageous physical and pharmaceutical properties.

(S)-3-(4-((4-(morpholinomethyl)benzyl)oxy)-1-oxoisoindolin-2-yl)piperidine-2,6-dione ("Compound A"), which is also known as CC-220, is an immunomodulatory compound that markedly inhibits TNF-α, IL-1β, and other inflammatory cytokines in LPS-stimulated hPBMC and human whole blood. TNF-α is an inflammatory cytokine produced by macrophages and monocytes during acute inflammation and is responsible for a diverse range of signaling events within cells. TNF-α may play a pathological role in cancer, inflammatory and immune-related diseases. Without being limited by theory, one of the biological effects exerted by Compound A is the reduction of synthesis of TNF-α. Compound A enhances the degradation of TNF-α mRNA and also potently inhibits IL-1β and stimulates IL-10 under these conditions. Further, without being limited by any particular theory, Compound A is a potent co-stimulator of T cells and increases cell proliferation in a dose dependent manner under appropriate conditions. In addition, without being limited by theory, the biological effects exerted by Compound A includes, but are not limited to, anti-angiogenic and immune modulating effects.

(S)-3-(4-((4-(morpholinomethyl)benzyl)oxy)-1-oxoisoindolin-2-yl)piperidine-2,6-dione and methods of preparing the same are described, e.g., in U.S. Patent Publication No. 2011/0196150, the entirety of which is incorporated herein by reference. Compound A has the following structure:

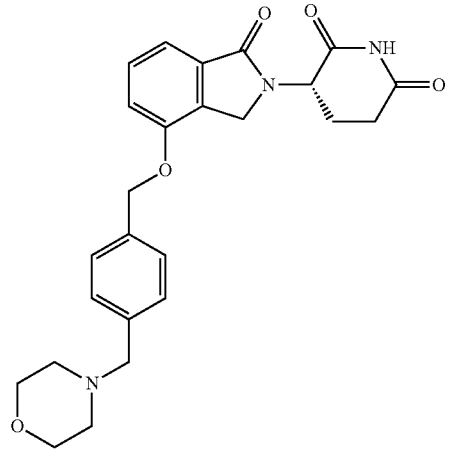

Compound A

Due to its diversified pharmacological properties, Compound A is useful in treating, preventing, and/or managing various diseases or disorders. However, Compound A is prone to hydrolysis and poses chemical stability challenges. Therefore, a need exists as to dosage forms of Compound A having advantageous physical and pharmaceutical properties.

3. SUMMARY

Provided herein are pharmaceutical dosage forms of Compound A, or a pharmaceutically acceptable prodrug, salt, solvate, hydrate, clathrate, stereoisomer, tautomer, or racemic mixtures thereof.

Also provided herein are methods of treating, managing, ameliorating and/or preventing diseases, disorders and/or conditions associated with immune-related and inflammatory diseases comprising administering a therapeutically effective amount of Compound A, or a pharmaceutically acceptable prodrug, salt, solvate, hydrate, clathrate, stereoisomer, tautomer or racemic mixtures thereof, in the dosage forms described herein.

Examples of inflammatory and immune-related diseases or disorders which may be treated, managed, or prevented by administering a therapeutically, or prophylactically, effective amount of Compound A, or a pharmaceutically acceptable prodrug, salt, solvate, hydrate, clathrate, stereoisomer, tautomer or racemic mixtures thereof in the dosage forms described herein, include, but are not limited to, lupus, scleroderma, lupus pernio, sarcoidosis, Sjögren syndrome, ANCA-induced vasculitis, anti-phospholipid syndrome, myasthenia gravis, Sjögren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroditis), idiopathic pulmonary fibrosis, idiopathic thrombocytopenia purpura, IgA nephropathy, juvenile arthritis, lichen planus, Ménière disease, mixed connective tissue disease, morephea, narcolepsy, neuromyotonia, pediatric autoimmune neuropsychiatric disorders (PANDAs), pemphigus vulgaris, pernicious anemia, polyarteritis nodosa, polychondritis, polymyalgia rheumatica, primary agammaglobulinemia, primary biliary cirrhosis, Raynaud disease (Raynaud phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, and/or Wegener's granulomatosis.

Also provided herein are methods of treating, managing, ameliorating and/or preventing cancer, including primary and metastatic cancer, as well as cancer that is refractory, relapsed or resistant to conventional chemotherapy, which comprise administering to a patient in need of such treatment or prevention a therapeutically or prophylactically effective amount of (S)-3-(4-((4-(morpholinomethyl)benzyl)oxy)-1-oxoisoindolin-2-yl)piperidine-2,6-dione, i.e., Compound A, in the dosage forms described herein.

In certain embodiments, provided herein are methods for the treatment or management of lymphoma, multiple myeloma, leukemia, and solid tumors.

In some embodiments, the lymphoma is selected from the group consisting of Hodgkin's lymphoma, non-Hodgkin's lymphoma, AIDS-related lymphomas, anaplastic large-cell lymphoma, angioimmunoblastic lymphoma, blastic NK-cell lymphoma, Burkitt's lymphoma, Burkitt-like lymphoma (small non-cleaved cell lymphoma, small lymphocytic lymphoma, cutaneous T-cell lymphoma, diffuse large B-cell Lymphoma, enteropathy-type T-cell lymphoma, lymphoblastic lymphoma, mantle cell lymphoma, marginal zone lymphoma, nasal T-cell lymphoma, pediatric lymphoma, peripheral T-cell lymphomas, primary central nervous system lymphoma, transformed lymphomas, treatment-related T-cell lymphomas and Waldenstrom's macroglobulinemia.

In some embodiments, the leukemia is selected from the group consisting of acute myeloid leukemia (AML), T-cell leukemia, chronic myeloid leukemia (CML), chronic lymphocytic leukemia (CLL) and acute lymphoblastic leukemia (ALL).

In some embodiments, the solid tumor is selected from the group consisting of melanoma, head and neck tumors, breast carcinoma, non-small cell lung carcinoma, ovarian carcinoma, pancreatic carcinoma, prostate carcinoma, colorectal carcinoma, and hepatocellular carcinoma.

In some embodiments, the cancer is advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage 1V non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

Compound A of the invention, or a pharmaceutically acceptable prodrug, salt, solvate, hydrate, clathrate, stereoisomer, tautomer, or racemic mixtures thereof, is intended for use in the treatment of all diseases, disorders or conditions disclosed herein.

3.1. Definitions

As used herein and unless otherwise indicated, a composition that is "substantially free" of a compound means that the composition contains less than about 20 percent by weight, preferably less than about 15 percent by weight, more preferably less than about 10 percent by weight, more preferably less than about 7 percent by weight, even more preferably less than about 5 percent by weight, and most preferably less than about 3 percent by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80 percent by weight of one stereoisomer of the compound and less than about 20 percent by weight of other stereoisomers of the compound, preferably greater than about 85 percent by weight of one stereoisomer of the compound and less than about 15 percent by weight of the other stereoisomers of the compound more preferably greater than about 90 percent by weight of one stereoisomer of the compound and less than about 10 percent by weight of the other stereoisomers of the compound, even more preferably greater than about 95 percent by weight of one stereoisomer of the compound and less than about 5 percent by weight of the other stereoisomers of the compound, and most preferably greater than about 97 percent by weight of one stereoisomer of the compound and less than about 3 percent by weight of the other stereoisomers of the compound.

As used herein and unless otherwise indicated, the term "enantiomerically pure" means a stereomerically pure composition of a compound having one chiral center.

As used herein and unless otherwise indicated, the term "racemic mixture" refers to an equimolar mixture of a pair of enantiomers.

As used herein, unless otherwise specified, the term "pharmaceutically acceptable salt(s)," as used herein includes, but is not limited to, salts of acidic or basic moieties of thalidomide. Basic moieties are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein, and unless otherwise specified, the term "tautomers" refers to constitutional isomers of a compound provided herein or a salt thereof that are readily intercovertible. A compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

As used herein, and unless otherwise specified, the term "clathrate" refers a to an inclusion compound in which a compound provided herein or a salt thereof is in a cage formed by a host molecule or by a lattice of host molecules.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of thalidomide that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of thalidomide that include —NO, —NO$_2$, —ONO, or —ONO$_2$ moieties. As used herein and unless otherwise indicated, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound, but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound, but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "biohydrolyzable ester" means an ester of a compound that either: 1) does not interfere with the biological activity of the compound, but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein and unless otherwise indicated, the term "biohydrolyzable amide" means an amide of a compound that either: 1) does not interfere with the biological activity of the compound, but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, and unless otherwise specified, the terms "treat," "treating" and "treatment" contemplate an action that occurs while a patient is suffering from the specified disease or disorder, which reduces the severity of the disease or disorder, or retards or slows the progression of the disease or disorder.

As used herein, and unless otherwise specified, the terms "prevent," "preventing" and "prevention" refer to the prevention of the onset, recurrence or spread of a disease or disorder, or of one or more symptoms thereof. The terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, and unless otherwise specified, the term "stable," when used in connection with a formulation or a dosage form, means that the active ingredient of the formulation or dosage form remains in its desired form, e.g., it remains solubilized for a specified amount of time and does not significantly degrade or aggregate or become otherwise modified (e.g., as determined, for example, by HPLC). In some embodiments, about 70 percent or greater, about 80 percent or greater or about 90 percent or greater of the compound remains solubilized after the specified period. As used herein, and unless otherwise specified, the term "method of treating, managing, ameliorating and/or preventing diseases, disorders and/or conditions as described below comprising administering a therapeutically or prophylactically effective amount of compound A, or a pharmaceutically acceptable prodrug, salt, solvate, hydrate, clathrate, stereoisomer, tautomer, or racemic mixture thereof" also means that a therapeutically or prophylactically effective amount of compound A, or a pharmaceutically acceptable prodrug, salt, solvate, hydrate, clathrate, stereoisomer, tautomer, or racemic mixture thereof can be used for a method of treating, managing, ameliorating and/or preventing diseases, disorders and/or conditions as described below.

4. DETAILED DESCRIPTION

Provided herein are pharmaceutical compositions and dosage forms of Compound A, or a pharmaceutically acceptable prodrug, salt, solvate, hydrate, clathrate, stereoisomer, tautomer, or racemic mixture thereof. In some embodiments, the compositions and dosage forms are suitable for oral administration to a patient. In other embodiments, the compositions and dosage forms provided herein exhibit advantageous physical and/or pharmacological properties. Such properties include, but are not limited to, ease of assay, content uniformity, flow properties for manufacture, dissolution and bioavailability, and stability. In certain embodiments, the compositions and dosage forms provided herein have a shelf life of at least about 6 months, at least about 12 months, at least about 18 months, at least about 24 months, at least about 30 months, or at least about 36 months without refrigeration. In certain embodiments, "without refrigeration" refers to a temperature at or above 20° C.

Also provided herein are kits comprising pharmaceutical compositions and dosage forms provided herein. Also provided herein are methods of treating, managing, and/or preventing a disease or disorder, which comprises administering to a patient in need thereof a pharmaceutical composition or a dosage form provided herein.

4.1 Compositions and Dosage Forms

In one embodiment, provided herein is a single unit dosage form suitable for oral administration to a human comprising: an amount equal to or greater than about 0.01, 0.02, 0.03, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 15, 17, 18 or 20 mg of an active ingredient; and a pharmaceutically acceptable excipient; wherein the active ingredient is Compound A, or a pharmaceutically acceptable prodrug, salt, solvate, clathrate, stereoisomer, tautomer, or racemic mixture thereof. In some embodiments, the amount of active ingredient is from about 0.01 to about 20 mg, from about 0.03 to about 15 mg, from about 0.05 to about 10 mg, from about 0.08 to about 5 mg, from about 0.1 mg to about 10 mg, from about 0.1 mg to about 2 mg, or from about 0.1 to about 1 mg. In one embodiment, the amount of the active ingredient is about 0.3 mg. In another embodiment, the amount of the active ingredient is about 0.1 mg. In another embodiment, the amount of the active ingredient is about 0.2 mg. In another embodiment, the amount of the active ingredient is about 0.3 mg. In another embodiment, the amount of the active ingredient is about 0.5 mg.

Pharmaceutical compositions and formulations provided herein can be presented as discrete dosage forms, such as capsules (e.g., gelcaps), caplets, tablets, troches, lozenges, dispersions, and suppositories each containing a predetermined amount of an active ingredient as a powder or in granules, a solution, or a suspension in an aqueous or non-aqueous liquid, an oil-in-water emulsion, or a water-in-oil liquid emulsion. Because of their ease of administration, tablets, caplets, and capsules represent a preferred oral dosage unit forms.

Tablets, caplets, and capsules typically contain from about 50 mg to about 500 mg of the pharmaceutical composition (i.e., active ingredient and excipient(s)). Capsules can be of any size. Examples of standard sizes include #000, #00, #0, #1, #2, #3, #4, and #5. See, e.g., *Remington's Pharmaceutical Sciences*, page 1658-1659 (Alfonso Gennaro ed., Mack Publishing Company, Easton Pa., 18th ed., 1990), which is incorporated by reference. In some embodiments, capsules provided herein are of size #1 or larger, #2 or larger, #3 or larger, or #4 or larger.

Also provided herein are anhydrous pharmaceutical compositions and dosage forms including an active ingredient, since water can facilitate the degradation of some compounds. For example, the addition of water (e.g., 5 percent) is widely accepted in the pharmaceutical arts as a means of simulating shelf-life, i.e., long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate decomposition. Thus, the effect of water on a formulation can be of great significance since moisture and/or humidity are commonly encountered during manufacture, handling, packaging, storage, shipment, and use of formulations. Without being limited by a particular theory, it was found that Compound A is easily degraded by hydrolysis, and thus, it is critical that all ingredients in the dosage forms are anhydrous or have a very low water content.

An anhydrous pharmaceutical compositions should be prepared and stored such that the anhydrous nature is maintained. Accordingly, in some embodiments, anhydrous compositions are packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, also provided herein is a method of preparing a solid pharmaceutical formulation including an active ingredient through admixing the active ingredient and an excipient under anhydrous or low moisture/humidity conditions, wherein the ingredients are substantially free of water. The method can further include packaging the anhydrous or non-hygroscopic solid formulation under low moisture conditions. By using such conditions, the risk of contact with water is reduced and the degradation of the active ingredient can be prevented or substantially reduced.

In one embodiment, Compound A, or a pharmaceutically acceptable prodrug, salt, solvate, clathrate, stereoisomer, tautomer, or racemic mixtures thereof, comprises from about 0.1 to about 10 weight percent of total weight of the composition. In another embodiment, Compound A, or a pharmaceutically acceptable prodrug, salt, solvate, clathrate, stereoisomer, tautomer, or racemic mixtures thereof, comprises from about 0.1 to about 5 weight percent of total weight of the composition. In another embodiment, Compound A, or a pharmaceutically acceptable prodrug, salt, solvate, clathrate, stereoisomer, tautomer, or racemic mixtures thereof, comprises from about 0.1 to about 3 weight percent of total weight of the composition. In another embodiment, Compound A, or a pharmaceutically acceptable prodrug, salt, solvate, clathrate, stereoisomer, tautomer, or racemic mixtures thereof, comprises from about 0.1 to about 3 weight percent of total weight of the composition. In another embodiment, Compound A, or a pharmaceutically acceptable prodrug, salt, solvate, clathrate, stereoisomer, tautomer, or racemic mixtures thereof, comprises from about 0.1 to about 1 weight percent of total weight of the composition. In another embodiment, Compound A, or a pharmaceutically acceptable prodrug, salt, solvate, clathrate, stereoisomer, tautomer, or racemic mixtures thereof, comprises from about 0.1 to about 0.5 weight percent of total weight of the composition. In another embodiment, Compound A, or a pharmaceutically acceptable prodrug, salt, solvate, clathrate, stereoisomer, tautomer, or racemic mixtures thereof, comprises about 0.1 weight percent of total weight of the composition. In another embodiment, Compound A, or a pharmaceutically acceptable prodrug, salt, solvate, clathrate, stereoisomer, tautomer, or racemic mixtures thereof, comprises from about 0.14 weight percent of total weight of the composition. In another embodiment, Compound A, or a pharmaceutically acceptable prodrug, salt, solvate, clathrate, stereoisomer, tautomer, or racemic mixtures thereof, comprises from about 0.144 weight percent of total weight of the composition. In another embodiment, Compound A, or a pharmaceutically acceptable prodrug, salt, solvate, clathrate, stereoisomer, tautomer, or racemic mixtures thereof, comprises about 0.4 weight percent of total weight of the composition. In another embodiment, Compound A, or a pharmaceutically acceptable prodrug, salt, solvate, clathrate, stereoisomer, tautomer, or racemic mixtures thereof thereof, comprises from about 0.43 weight percent of total weight of the composition. In another embodiment, Compound A, or a pharmaceutically acceptable prodrug, salt, solvate, clathrate, stereoisomer, tautomer, or racemic mixtures thereof, comprises from about 0.432 weight percent of total weight of the composition.

In one embodiment, the active ingredient and carrier, diluent, binder, or filler are directly blended as described herein elsewhere. In another embodiment, the carrier, diluent, binder, or filler comprises lactose and/or starch. In one embodiment, the lactose is anhydrous lactose. In another embodiment, the starch is pregelatinized starch.

In one embodiment, the carrier, diluent, binder, or filler comprises from about 70 to about 99.9 weight percent of total weight of the composition. In another embodiment, the carrier, diluent, binder, or filler comprises from about 80 to about 99.9 weight percent of total weight of the composition. In another embodiment, the carrier, diluent, binder, or filler comprises from about 85 to about 99.9 weight percent of total weight of the composition. In another embodiment, the carrier, diluent, binder, or filler comprises from about 90 to about 99.9 weight percent of total weight of the composition. In another embodiment, the carrier, diluent, binder, or filler comprises from about 95 to about 99.9 weight percent of total weight of the composition. In another embodiment, the carrier, diluent, binder, or filler comprises about 99 to about 99.9 weight percent of total weight of the composition. In another embodiment, the carrier, diluent, binder, or filler comprises about 99.6 weight percent of total weight of the composition. In another embodiment, the carrier, diluent, binder, or filler comprises about 99.9 weight percent of total weight of the composition.

In one embodiment, the dosage forms provided herein comprise both lactose and starch. In one embodiment, lactose and starch comprise from about 70 to about 99.5 weight percent of total weight of the composition. In another embodiment, lactose and starch comprise from about 80 to about 99.5 weight percent of total weight of the composition. In another embodiment, lactose and starch comprise from about 85 to about 99 weight percent of total weight of the composition. In another embodiment, lactose and starch comprise from about 90 to about 99.5 weight percent of total weight of the composition. In another embodiment, lactose and starch comprise from about 95 to about 99.3 weight percent of total weight of the composition. In another embodiment, lactose and starch comprise about 99 to about 99.5 weight percent of total weight of the composition. In another embodiment, lactose and starch comprise about 99.3 weight percent of total weight of the composition. In another embodiment, lactose and starch comprise about 99.5 weight percent of total weight of the composition.

In one embodiment, the ratio of lactose:starch in the dosage form is from about 1:1 to about 5:1. In one embodiment, the ratio of lactose:starch in the dosage form is about 3:1.

In another embodiment, the dosage form comprises a lubricant. In one embodiment, the dosage form comprises about 0.2 mg of lubricant. In another embodiment, the dosage form comprises about 0.22 mg of lubricant. In another embodiment, the dosage form comprises 0.225 mg of lubricant. In one embodiment, the lubricant is stearic acid.

In another embodiment, the dosage form comprises a lubricant. In one embodiment, the dosage form comprises about 0.4 mg of lubricant. In another embodiment, the dosage form comprises about 0.37 mg of lubricant. In another embodiment, the dosage form comprises 0.375 mg of lubricant. In another embodiment, the dosage form comprises about 0.45 mg of lubricant. In one embodiment, the lubricant is stearic acid.

In one embodiment, the lubricant, e.g., stearic acid, comprises from about 0.01 to about 5 weight percent of total weight of the composition. In another embodiment, the lubricant, e.g., stearic acid, comprises from about 0.01 to about 1 weight percent of total weight of the composition. In another embodiment, the lubricant, e.g., stearic acid, comprises from about 0.1 to about 1 weight percent of total weight of the composition. In another embodiment, the lubricant, e.g., stearic acid, comprises from about 0.1 to about 0.5 weight percent of total weight of the composition. In another embodiment, the lubricant, e.g., stearic acid, comprises from about 0.2 to about 0.3 weight percent of total weight of the composition. In another embodiment, the lubricant, e.g., stearic acid, comprises about 0.3 weight percent of total weight of the composition.

In some embodiments, because it is typical to obtain Compound A, or a pharmaceutically acceptable prodrug, salt, solvate, clathrate, stereoisomer, tautomer, or racemic mixtures thereof, at a purity of less than 100%, the formulations and dosage forms provided herein may be defined as compositions, formulations, or dosage forms that comprise Compound A, or a pharmaceutically acceptable prodrug, salt, solvate, clathrate, stereoisomer, tautomer, or racemic mixtures thereof, at an amount that provides the potency of a specified amount of 100% pure Compound A.

For example, in one embodiment, provided herein is a single unit dosage form comprising: 1) Compound A, or a pharmaceutically acceptable prodrug, salt, solvate, clathrate, stereoisomer, tautomer, or racemic mixtures thereof, present at an amount that provides about 0.3 mg potency of Compound A; and 2) about 74.7 mg of a carrier, diluent, binder, or filler, respectively. In one embodiment, the amount of a carrier, diluent, binder, or filler is about 75 mg.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.3 mg potency of Compound A; and 2) a pharmaceutically acceptable excipient. In one embodiment, the total weight of the dosage form is about 75 mg. In one embodiment, the dosage form is suitable for administration in a size #4 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 75 mg, the carrier, diluent, binder, or filler comprises lactose and/or starch. In one embodiment, the excipient comprises both lactose and starch. In one embodiment, where both lactose and starch are present in the dosage form, the dosage form comprises about 18.075 mg of starch, and the remaining weight is filled by lactose. In one embodiment, the lactose is anhydrous lactose. In another embodiment, the starch is pregelatinized starch.

In one embodiment where the total weight of the dosage form is about 75 mg and where a lubricant is present, the lubricant is stearic acid. In one embodiment, the stearic acid is present at an amount of about 0.2 mg. In one embodiment, the stearic acid is present at an amount of about 0.225 mg.

In one embodiment, provided herein is a dosage form comprising: 1) Compound A, or a pharmaceutically acceptable stereoisomer, prodrug, salt, solvate, or clathrate thereof, present at an amount that provides about 0.3 mg potency of Compound A; 2) about 18.075 mg of pregelatinized starch; 3) about 0.225 mg of stearic acid; and 4) anhydrous lactose at an amount that brings the total weight of the dosage form to 75 mg. In one embodiment, the dosage form is suitable for administration in a size #4 or larger capsule.

In one embodiment, provided herein is a single unit dosage form comprising: 1) Compound A, or a pharmaceutically acceptable prodrug, salt, solvate, clathrate, stereoisomer, tautomer, or racemic mixtures thereof, present at an amount that provides about 0.1 mg potency of Compound A; and 2) about 74.9 mg of a carrier, diluent, binder, or filler, respectively. In one embodiment, the amount of a carrier, diluent, binder, or filler is about 75 mg.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.1 mg potency of Compound A; and 2) a pharmaceutically acceptable excipient. In one embodiment, the total weight of the dosage form is about 75 mg. In one embodiment, the dosage form is suitable for administration in a size #4 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 75 mg, the carrier, diluent, binder, or filler comprises lactose and/or starch. In one embodiment, the excipient comprises both lactose and starch. In one embodiment, where both lactose and starch are present in the dosage form, the dosage form comprises about 18.75 mg of starch, and the remaining weight is filled by lactose. In one embodiment, the lactose is anhydrous lactose. In another embodiment, the starch is pregelatinized starch.

In one embodiment where the total weight of the dosage form is about 75 mg and where a lubricant is present, the lubricant is stearic acid. In one embodiment, the stearic acid is present at an amount of about 0.22 mg. In one embodiment, the stearic acid is present at an amount of about 0.225 mg.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.1 mg potency of Compound A; 2) about 18.75 mg of pregelatinized starch; 3) about 0.225 mg of stearic acid; and 4) anhydrous lactose at an amount that brings the total weight of the dosage form to 75 mg. In one embodiment, the dosage form is suitable for administration in a size #4 or larger capsule.

In one embodiment, provided herein is a single unit dosage form comprising: 1) Compound A, or a pharmaceutically acceptable prodrug, salt, solvate, clathrate, stereoisomer, tautomer, or racemic mixtures thereof, present at an amount that provides about 0.2 mg potency of Compound A; and 2) about 149.8 mg of a carrier, diluent, binder, or filler, respectively. In one embodiment, the amount of a carrier, diluent, binder, or filler is about 150 mg.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.2 mg potency of Compound A; and 2) a pharmaceutically acceptable excipient. In one embodiment, the total weight of the dosage form is about 150 mg. In one embodiment, the dosage form is suitable for administration in a size #3 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 150 mg, the carrier, diluent, binder, or filler comprises lactose and/or starch. In one embodiment, the excipient comprises both lactose and starch. In one embodiment, where both lactose and starch are present in the dosage form, the dosage form comprises about 37.5 mg of starch, and the remaining weight is filled by lactose. In one embodiment, the lactose is anhydrous lactose. In another embodiment, the starch is pregelatinized starch.

In one embodiment where the total weight of the dosage form is about 46.3 mg and where a lubricant is present, the lubricant is stearic acid. In one embodiment, the stearic acid is present at an amount of about 0.4 mg. In one embodiment, the stearic acid is present at an amount of about 0.45 mg.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.2 mg potency of Compound A; 2) about 37.5 mg of pregelatinized starch; 3) about 0.45 mg of stearic acid; and 4) anhydrous lactose at an amount that brings the total weight of the dosage form to 150 mg. In one embodiment, the dosage form is suitable for administration in a size #3 or larger capsule.

In one embodiment, provided herein is a single unit dosage form comprising: 1) Compound A, or a pharmaceutically acceptable prodrug, salt, solvate, clathrate, stereoisomer, tautomer, or racemic mixtures thereof, present at an amount that provides about 0.5 mg potency of Compound A; and 2) about 124.5 mg of a carrier, diluent, binder, or filler, respectively. In one embodiment, the amount of a carrier, diluent, binder, or filler is about 125 mg.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.5 mg potency of Compound A; and 2) a pharmaceutically acceptable excipient. In one embodiment, the total weight of the dosage form is about 125 mg. In one embodiment, the dosage form is suitable for administration in a size #3 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 125 mg, the carrier, diluent, binder, or filler comprises lactose and/or starch. In one embodiment, the excipient comprises both lactose and starch. In one embodiment, where both lactose and starch are present in the dosage form, the dosage form comprises about 31.25 mg of starch, and the remaining weight is filled by lactose. In one embodiment, the lactose is anhydrous lactose. In another embodiment, the starch is pregelatinized starch.

In one embodiment where the total weight of the dosage form is about 125 mg and where a lubricant is present, the lubricant is stearic acid. In one embodiment, the stearic acid is present at an amount of about 0.37 mg. In one embodiment, the stearic acid is present at an amount of about 0.375 mg.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.5 mg potency of Compound A; 2) about 31.25 mg of pregelatinized starch; 3) about 0.375 mg of stearic acid; and 4) anhydrous lactose at an amount that brings the total weight of the dosage form to 125 mg. In one embodiment, the dosage form is suitable for administration in a size #3 or larger capsule.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.432 weight percent of Compound A; and 2) a pharmaceutically acceptable excipient. In one embodiment, the excipient comprises a carrier, diluent, binder, or filler.

In one embodiment, the excipients comprise a carrier, diluent, binder, or filler and a lubricant.

In one embodiment where the total weight percent of Compound A is 0.432 percent, the carrier, diluent, binder, or filler comprises lactose and/or starch. In one embodiment, the excipient comprises both lactose and starch. In one embodiment, where both lactose and starch are present in the dosage form, the dosage form comprises about 25.0 weight percent of starch, and the remaining weight is filled by lactose. In one embodiment, the lactose is anhydrous lactose. In another embodiment, the starch is pregelatinized starch.

In one embodiment where the total weight percent of Compound A is 0.432 percent, and where a lubricant is present, the lubricant is stearic acid. In one embodiment, the stearic acid is present at a weight percent of 0.300 percent.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.432 weight percent of Compound A; 2) about 25.0 weight percent of pregelatinized starch; 3) about 0.300 weight percent of stearic acid; and 4) anhydrous lactose at an amount that brings the total weight percent to 100 percent.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.144 weight percent of Compound A; and 2) a pharmaceutically acceptable excipient. In one embodiment, the excipient comprises a carrier, diluent, binder, or filler. In one embodiment, the excipients comprise a carrier, diluent, binder, or filler and a lubricant.

In one embodiment where the total weight percent of Compound A is 0.144 percent, the carrier, diluent, binder, or filler comprises lactose and/or starch. In one embodiment, the excipient comprises both lactose and starch. In one embodiment, where both lactose and starch are present in the dosage form, the dosage form comprises about 25.0 weight percent of starch, and the remaining weight is filled by lactose. In one embodiment, the lactose is anhydrous lactose. In another embodiment, the starch is pregelatinized starch.

In one embodiment where the total weight percent of Compound A is 0.144 percent, and where a lubricant is present, the lubricant is stearic acid. In one embodiment, the stearic acid is present at a weight percent of 0.300 percent.

In one embodiment, provided herein is a dosage form comprising: 1) Compound A, or a pharmaceutically acceptable prodrug, salt, solvate, clathrate, stereoisomer, tautomer, or racemic mixtures thereof, present at an amount that provides about 0.432 weight percent of Compound A; 2) about 25.0 weight percent of pregelatinized starch; 3) about 0.300 weight percent of stearic acid; and 4) anhydrous lactose at an amount that brings the total weight percent to 100 percent.

In another embodiment, provided herein is a dosage form comprising Compound A, or a pharmaceutically acceptable prodrug, salt, solvate, clathrate, stereoisomer, tautomer, or racemic mixtures thereof, present at an amount that provides about 0.3 mg potency of Compound A, which is stable for a period of at least about 12, about 24, or about 36 months without refrigeration. In some embodiments, the dosage form comprises lactose and/or starch. In one embodiment where both starch and lactose are present in the dosage form, starch is present at an amount of about 18 mg, and lactose is present at an amount that brings the total weight of composition to about 75 mg. In some embodiments, the dosage form further comprises stearic acid at an amount of about 0.22 mg or about 0.225 mg. In some embodiments, provided herein is a dosage form comprising: 1) Compound A, or a pharmaceutically acceptable prodrug, salt, solvate, clathrate, stereoisomer, tautomer, or racemic mixtures thereof, present at an amount that provides about 0.3 mg potency of Compound A, about 18.075 mg pregelatinized starch; about 0.225 mg stearic acid; and anhydrous lactose at an amount that brings the total weight of the dosage form to 75 mg; wherein the dosage form is stable for a period of at least about 12, about 24, or about 36 months without refrigeration. In one embodiment, the dosage form is suitable for administration in a size 4 or larger capsule.

In another embodiment, provided herein is a dosage form comprising Compound A, or a pharmaceutically acceptable prodrug, salt, solvate, clathrate, stereoisomer, tautomer, or racemic mixtures thereof, present at an amount that provides about 0.1 mg potency of Compound A, which is stable for a period of at least about 12, about 24, or about 36 months without refrigeration. In some embodiments, the dosage form comprises lactose and/or starch. In one embodiment where both starch and lactose are present in the dosage form, starch is present at an amount of about 18.75 mg, and lactose is present at an amount that brings the total weight of composition to about 75 mg. In some embodiments, the dosage form further comprises stearic acid at an amount of about 0.22 mg or about 0.225 mg. In some embodiments, provided herein is a dosage form comprising: 1) Compound A, or a pharmaceutically acceptable prodrug, salt, solvate, clathrate, stereoisomer, tautomer, or racemic mixtures thereof, present at an amount that provides about 0.1 mg potency of Compound A, about 18.75 mg pregelatinized starch; about 0.225 mg stearic acid; and anhydrous lactose at an amount that brings the total weight of the dosage form to 75 mg; wherein the dosage form is stable for a period of at least about 12, about 24, or about 36 months without refrigeration. In one embodiment, the dosage form is suitable for administration in a size #4 or larger capsule.

In another embodiment, provided herein is a dosage form comprising Compound A, or a pharmaceutically acceptable prodrug, salt, solvate, clathrate, stereoisomer, tautomer, or racemic mixtures thereof, present at an amount that provides about 0.2 mg potency of Compound A, which is stable for a period of at least about 12, about 24, or about 36 months without refrigeration. In some embodiments, the dosage form comprises lactose and/or starch. In one embodiment where both starch and lactose are present in the dosage form, starch is present at an amount of about 37.5 mg, and lactose is present at an amount that brings the total weight of composition to about 150 mg. In some embodiments, the dosage form further comprises stearic acid at an amount of about 0.4 mg or about 0.45 mg. In some embodiments, provided herein is a dosage form comprising: 1) Compound A, or a pharmaceutically acceptable prodrug, salt, solvate, clathrate, stereoisomer, tautomer, or racemic mixtures thereof, present at an amount that provides about 0.2 mg potency of Compound A, about 37.5 mg pregelatinized starch; about 0.45 mg stearic acid; and anhydrous lactose at an amount that brings the total weight of the dosage form to 150 mg; wherein the dosage form is stable for a period of at least about 12, about 24, or about 36 months without refrigeration. In one embodiment, the dosage form is suitable for administration in a size #3 or larger capsule.

In another embodiment, provided herein is a dosage form comprising Compound A, or a pharmaceutically acceptable prodrug, salt, solvate, clathrate, stereoisomer, tautomer, or racemic mixtures thereof, present at an amount that provides about 0.5 mg potency of Compound A, which is stable for a period of at least about 12, about 24, or about 36 months without refrigeration. In some embodiments, the dosage form comprises lactose and/or starch. In one embodiment where both starch and lactose are present in the dosage form, starch is present at an amount of about 31.25 mg, and lactose is present at an amount that brings the total weight of composition to about 125 mg. In some embodiments, the dosage form further comprises stearic acid at an amount of about 0.37 mg or about 0.375 mg. In some embodiments, provided herein is a dosage form comprising: 1) Compound A, or a pharmaceutically acceptable prodrug, salt, solvate, clathrate, stereoisomer, tautomer, or racemic mixtures thereof, present at an amount that provides about 0.5 mg potency of Compound A, about 31.25 mg pregelatinized starch; about 0.375 mg stearic acid; and anhydrous lactose at an amount that brings the total weight of the dosage form to 125 mg; wherein the dosage form is stable for a period of at least about 12, about 24, or about 36 months without refrigeration. In one embodiment, the dosage form is suitable for administration in a size #3 or larger capsule.

4.1.1 Second Active Agents

In certain embodiments, provided herein are compositions and dosage form of Compound A, or a pharmaceutically acceptable prodrug, salt, solvate, clathrate, stereoisomer, tautomer, or racemic mixtures thereof, which may further comprise one or more secondary active ingredients. Certain combinations may work synergistically in the treatment of particular types diseases or disorders, and conditions and symptoms associated with such diseases or disorders. Compound A, or a pharmaceutically acceptable prodrug, salt, solvate, clathrate, stereoisomer, tautomer, or racemic mixtures thereof, can also work to alleviate adverse effects associated with certain second active agents, and vice versa.

Specific second active compounds that can be contained in the formulations and dosage forms provided herein vary depending on the specific indication to be treated, prevented or managed.

For instance, for the treatment, prevention or management of the disease, disorder or condition as mentioned under section 3, e.g., cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Yet other second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0214328, 2005/0239842, 2006/0154880, 2006/0122228, and 2005/0143344; and U.S. provisional application No. 60/631,870.

Examples of second active agents that may be used for the treatment, prevention and/or management of the disease, disorder or condition as mentioned under section 3, e.g. of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the Physician's Desk Reference 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine) (Tegretol®, oxcarbazepine (Trileptar), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16, 17-1-methylethylidinebis (oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hypertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Clalis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interferon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

4.2. Process for Making Dosage Forms

Dosage forms provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms provided herein can be done using capsules of methylcellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process.

Direct blend formulations may be advantageous in certain instances because they require only one blending step, that of the active and excipients, before being processed into the final dosage form, e.g., tablet or capsule. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

4.2.1. Screening

The process for making the pharmaceutical compositions of the invention preferably includes the screening of the active ingredient(s) and the excipient(s). In one embodiment, the active ingredient is passed through a screen having openings of about 200 microns to about 750 microns. In another embodiment, the active ingredient is passed through a screen with openings of about 200 microns to about 400 microns. In one embodiment, the active ingredient is passed through a screen having openings of about 300 to qbout 400 microns. Depending on the excipient(s) used, the screen openings vary. For example, disintegrants and binders are passed through openings of about 430 microns to about 750 microns, from about 600 microns to about 720 microns, or about 710 microns. Lubricants are typically passed through smaller openings, e.g., about 150 microns to about 250 microns screen. In one embodiment, the lubricant is passed through a screen opening of about 210 microns.

4.2.2. Pre-Blending

After the ingredients are screened, the excipient(s) and active ingredient(s) are mixed in a diffusion mixer. In one embodiment, the mixing time is from about 1 minute to about 50 minutes, from about 5 minutes to about 45 minutes, from about 10 minutes to about 40 minutes, from about 10 minutes to about 30 minutes, or from about 10 minutes to about 25 minutes. In another embodiment, the mixing time is about 15 minutes.

When more than one excipients are used, the excipients may be admixed in a tumble blender for about 1 minute to about 20 minutes, or for about 5 minutes to about 10 minutes, prior to mixing with the active ingredient.

4.2.3. Roller Compaction

In one embodiment, the pre-blend may optionally be passed through a roller compactor with a hammer mill attached at the discharge of the compactor.

4.2.4. Final Blend

When a lubricant, e.g., stearic acid, is used, the lubricant is mixed with the pre-blend at the end of the process to complete the pharmaceutical composition. This additional mixing is from about 1 minute to about 10 minutes, or from about 3 minutes to about 5 minutes.

4.2.5. Encapsulation

The formulation mixture is then encapsulated into the desired size capsule shell using, for example, a capsule filling machine or a rotary tablet press.

4.3. Kits

Pharmaceutical packs or kits which comprise pharmaceutical compositions or dosage forms provided herein are also provided. An example of a kit comprises notice in the form prescribed by a governmental agency regulating the manufacture, use or sale of pharmaceuticals or biological products, which notice reflects approval by the agency of manufacture, use or sale for human administration.

4.4 Methods of Treatment, Prevention, and Management

Provided herein are methods of treating, preventing, and/or managing diseases, disorders and/or conditions associated with immune-related and inflammatory diseases comprising administering a therapeutically effective amount of Compound A, or a pharmaceutically acceptable salt, solvate, hydrate, clathrate, stereoisomer, tautomer or racemic mixtures thereof to a patient in need thereof. In certain embodiments, the disease or disorder is selected from lupus, scleroderma, Sjögren syndrome, ANCA-induced vasculitis, antiphospholipid syndrome and myasthenia gravis. In certain embodiments, the disease or disorder is lupus or scleroderma.

The sensitivity of Compound A, or a pharmaceutically acceptable salt, solvate, hydrate, clathrate, stereoisomer, tautomer or racemic mixtures thereof can be studied in various in vivo and in vitro assays, including animal models known to one of skill in the art for immune-related and inflammatory diseases, including, but not limited to MRL/MpJ-Faslpr/J mouse model of systemic lupus erythematosus, NZBWF1/J mouse model of systemic lupus erythematosus, bleomycin-induced skin fibrosis model, and murine tight skin-1 (Tsk-1) mouse model.

4.4.1 Treatment of Scleroderma

In certain embodiments, provided herein are methods of treating, preventing, and/or managing scleroderma or a symptom thereof, comprising administering a therapeutically effective amount of Compound A, or a pharmaceutically acceptable salt, solvate, hydrate, clathrate, stereoisomer, tautomer or racemic mixtures thereof to a patient having scleroderma.

In certain embodiments, provided herein are methods of preventing scleroderma or a symptom thereof, comprising administering an effective amount of Compound A, or a pharmaceutically acceptable salt, solvate, hydrate, clathrate, stereoisomer, tautomer or racemic mixtures thereof to a patient at risk of having scleroderma.

In certain embodiments, the scleroderma is localized, systemic, limited or diffuse scleroderma.

In certain embodiments, the systemic scleroderma comprises CREST syndrome (Calcinosis, Raynaud's syndrome, esophagaeal dysfunction or dysmotility, sclerodactyl), telangiectasia). Scleroderma is also known as systemic sclerosis or progressive systemic sclerosis. In certain embodiments, provided herein are methods of treating or preventing Raynaud's disease or syndrome. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited scleroderma is limited to the hands, the face, neck, or combinations thereof.

In certain embodiments, diffuse scleroderma comprises skin tightening and also occurs above the wrists (or elbows). In certain embodiments, the diffuse systemic sclerosis can be sine scleroderma, comprising internal organ fibrosis, but no skin tightening; or familial progressive systemic sclerosis.

In one embodiment, scleroderma is not associated with wasting, such as disease-related wasting.

In one embodiment, provided herein are methods for the reduction, inhibition, or prevention of one or more of the following symptoms of scleroderma: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophagaeal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; or (xx) digital autoamputation, comprising administering an effective amount of Compound A to a patient in need thereof.

Without being bound to any particular theory, it is believed that Compound A, or a pharmaceutically acceptable salt, solvate, hydrate, clathrate, stereoisomer, tautomer or racemic mixtures thereof enhances Th1 immune response, and suppresses Th2 immune response, which may result in anti-fibrotic effects in the skin.

Further provided herein are methods for improving or reducing the skin thickness of a patient having scleroderma comprising administering an effective amount of Compound A, or a pharmaceutically acceptable salt, solvate, hydrate, clathrate, stereoisomer, tautomer or racemic mixtures thereof to the patient. In one embodiment, the skin thickness is reduced by about 20%, about 25%, about 30%, about 40%, about 50%, about 60%, about 70%, about 80%, about 90% or more. In one embodiment, the skin thickness is reduced by about 20%, about 25%, about 30%, or about 40%. In one embodiment, the skin thickness is reduced by about 50%, about 60%, about 70%, about 80%, about 90% or more.

Further provided herein are methods for achieving one or more clinical endpoints associated with scleroderma comprising administering an effective amount of Compound A, or a pharmaceutically acceptable salt, solvate, hydrate, clathrate, stereoisomer, tautomer or racemic mixtures thereof to a patient in need thereof.

Further provided herein are methods for increasing the overall survival, objective response rate, time to progression, progression-free survival and/or time-to-treatment failure of a patient having scleroderma comprising administering an effective amount of Compound A, or a pharmaceutically acceptable salt, solvate, hydrate, clathrate, stereoisomer, tautomer or racemic mixtures thereof to the patient.

Further provided herein are methods for decreasing mortality, respiratory mortality and/or respiratory hospitalization of a patient having scleroderma comprising administering an effective amount of Compound A, or a pharmaceutically acceptable salt, solvate, hydrate, clathrate, stereoisomer, tautomer or racemic mixtures thereof to the patient.

Further provided herein are methods for improving the modified Rodnan skin score of a patient having scleroderma comprising administering an effective amount of Compound A, or a pharmaceutically acceptable salt, solvate, hydrate, clathrate, stereoisomer, tautomer or racemic mixtures thereof to the patient. In one embodiment, the improvement in modified Rodnan skin score is 5, 10, 15 or 20 points or more.

Further provided herein are methods for improving or reducing skin induration of a patient having scleroderma comprising administering an effective amount of Compound A, or a pharmaceutically acceptable salt, solvate, hydrate, stereoisomer, tautomer or racemic mixtures thereof to the patient.

Further provided herein are methods for improving the dermatology quality of life index of a patient having scleroderma comprising administering an effective amount of Compound A, or a pharmaceutically acceptable salt, solvate, hydrate, clathrate, stereoisomer, tautomer or racemic mixtures thereof to the patient.

Further provided herein are methods for improving the pulmonary function of a patient having scleroderma comprising administering an effective amount of Compound A, or a pharmaceutically acceptable salt, solvate, hydrate, clathrate, stereoisomer, tautomer or racemic mixtures thereof to the patient.

Further provided herein are methods for improving the carbon monoxide diffusing capacity of a patient having scleroderma comprising administering an effective amount of Compound A, or a pharmaceutically acceptable salt, solvate, hydrate, clathrate, stereoisomer, tautomer or racemic mixtures thereof to the patient. In one embodiment, the carbon monoxide diffusing capacity of a patient is improved by an improvement in the diffusing capacity of the lung for carbon monoxide ($D_L co$) of about 10%, about 20%, about 25%, about 30%, about 40%, about 50%, about 60%, about 70% about 80%, about 90% or more.

Further provided herein are methods for improving the Mahler Dyspnea index of a patient having scleroderma comprising administering an effective amount of Compound A, or a pharmaceutically acceptable salt, solvate, hydrate, clathrate, stereoisomer, tautomer or racemic mixtures thereof to the patient. In one embodiment, the improvement in Mahler Dyspnea index is 4, 5, 6, 7, 8, 9 or 10 points or more.

Further provided herein are methods for improving the Saint George's Respiratory Questionnaire score of a patient having scleroderma comprising administering an effective amount of Compound A, or a pharmaceutically acceptable salt, solvate, hydrate, clathrate, stereoisomer, tautomer or racemic mixtures thereof to the patient. In one embodiment, the improvement in Saint George's Respiratory Questionnaire score is 4, 8, 12, 16, 20, 24, 28, 32, 36, 40, 44, 48, 52 points or more.

Further provided herein are methods for improving the UCLA scleroderma clinical trial consortium gastrointestinal tract score of a patient having scleroderma comprising administering an effective amount of Compound A, or a pharmaceutically acceptable salt, solvate, hydrate, clathrate, stereoisomer, tautomer or racemic mixtures thereof to the patient. Determination of the UCLA scleroderma clinical trial consortium gastrointestinal tract score of a patient is described, e.g., by Khanna, D. et al, *Arthritis & Rheumatism*, 2009, 61: 1257-1263.

Further provided herein are methods for treating or preventing digital ulcer of a patient or patient population having scleroderma comprising administering an effective amount of Compound A, or a pharmaceutically acceptable salt, solvate, hydrate, clathrate, stereoisomer, tautomer or racemic mixtures thereof to the patient.

Further provided herein are methods improving flow-mediated dilatation of a patient having scleroderma comprising administering an effective amount of Compound A, or a pharmaceutically acceptable salt, solvate, hydrate, clathrate, stereoisomer, tautomer or racemic mixtures thereof to the patient.

Further provided herein are methods improving or increasing the six minute walk distance of a patient having scleroderma comprising administering an effective amount of Compound A, or a pharmaceutically acceptable salt, solvate, hydrate, clathrate, stereoisomer, tautomer or racemic mixtures thereof to the patient. In one embodiment, the improvement in the six minute walk distance is about 200 meters, about 250 meters, about 300 meters, about 350 meters, about 400 meters or more.

4.4.2 Treatment of Lupus Erythematosus

In certain embodiments, provided herein are methods of treating, preventing, and/or managing lupus erythematosus or a symptom thereof, comprising administering a therapeutically effective amount of Compound A, or a pharmaceutically acceptable salt, solvate, hydrate, clathrate, stereoisomer, tautomer or racemic mixtures thereof to a patient having lupus erythematosus.

In one embodiment, provided herein are methods of preventing lupus erythematosus or a symptom thereof, comprising administering an effective amount of Compound A, or a pharmaceutically acceptable salt, solvate, hydrate, clathrate, stereoisomer, tautomer or racemic mixtures thereof to a patient at risk of having lupus erythematosus.

In certain embodiments, provided herein are methods for treating, preventing, and/or managing systemic lupus erythematosus (SLE), cutaneous lupus erythematosus (CLE) or drug-induced lupus.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In:

*Harrison's Principles of Internal Medicine* (16th edition). New York (US): McGraw-Hill; 2005. pp. 1960-1967).

Symptoms of SLE vary from person to person, and may come and go. In most patients, the symptoms include joint pain and swelling. Frequently affected joints are the fingers, hands, wrists, and knees. Some patients develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash—a "butterfly" rash over the cheeks and bridge of the nose affects about half of people with SLE, in some patients, the rash gets worse in sunlight, and the rash may also be widespread.

Other symptoms depend on what part of the body is affected, and may include the following:

Brain and nervous system: headaches, numbness, tingling, seizures, vision problems, personality changes,
Digestive tract: abdominal pain, nausea, and vomiting,
Heart: abnormal heart rhythms (arrhythmias),
Lung: coughing up blood and difficulty breathing, and
Skin: patchy skin color, fingers that change color when cold (Raynaud's phenomenon).

Some patients only have skin symptoms. This is called discoid lupus.

In one embodiment, provided herein are methods of treating moderate, severe, or very severe SLE. The term "severe SLE" as used herein refers to an SLE condition where the patient has one or more severe or life-threatening symptoms (such as hemolytic anemia, extensive heart or lung involvement, kidney disease, or central nervous system involvement).

Further provided herein are methods for achieving one or more clinical endpoints associated with SLE comprising administering an effective amount of Compound A, or a pharmaceutically acceptable salt, solvate, hydrate, clathrate, stereoisomer, tautomer or racemic mixtures thereof to a patient in need thereof.

Further provided herein are methods for increasing the overall survival, objective response rate, time to progression, progression-free survival and/or time-to-treatment failure of a patient having SLE comprising administering an effective amount of Compound A, or a pharmaceutically acceptable salt, solvate, hydrate, clathrate, stereoisomer, tautomer or racemic mixtures thereof to the patient.

In certain embodiment, Compound A, or a pharmaceutically acceptable salt, solvate, hydrate, clathrate, stereoisomer, tautomer or racemic mixtures thereof acts as an inhibitor of primary human memory CD19+ B-cell differentiation to the plasmablast stage. Without being bound to any particular theory, it is believed that Compound A, or a pharmaceutically acceptable salt, solvate, hydrate, clathrate, stereoisomer, tautomer or racemic mixtures thereof blocks cells at a premature stage thereby decreasing the numbers of plasmablasts that are capable of producing high levels of immunoglobulin. A functional consequence of this effect is reduced immunoglobulin G (IgG) and immunoglobulin M (IgM) production in these differentiation cultures.

In certain embodiments, Compound A, or a pharmaceutically acceptable salt, solvate, hydrate, clathrate, stereoisomer, tautomer or racemic mixtures thereof inhibits of the ability of primary human memory CD19+ B-cells to differentiate to the plasmablast stage. In certain embodiments, Compound A, or a pharmaceutically acceptable salt, solvate, hydrate, clathrate, stereoisomer, tautomer or racemic mixtures thereof has no significant effect on mature CD138+ plasma cells in short term cultures. In certain embodiments, Compound A, or a pharmaceutically acceptable salt, solvate, hydrate, clathrate, stereoisomer, tautomer or racemic mixtures thereof inhibits B cell differentiation factors including interferon regulatory factor 4 (IRF4), lymphocyte-induced maturation protein (BLIMP), X-box-protein-1 (XBP-1) and B cell lymphoma 6 (Bcl6).

4.4.3 Treatment of Other Immune-Related Diseases or Disorders

Further provided herein are methods of treating, managing, or preventing other immune-related diseases or conditions using Compound A, or a pharmaceutically acceptable salt, solvate, hydrate, clathrate, stereoisomer, tautomer or racemic mixtures thereof. In certain embodiments, for example, provided herein is a method of treating an individual having a disease or disorder, wherein the disease or disorder is caused by, or is associated with, an inappropriate or undesirable immune response, e.g., a disease, disorder or condition that can be treated beneficially by immunosuppression, comprising administering to the individual Compound A, or a pharmaceutically acceptable salt, solvate, hydrate, clathrate, stereoisomer, tautomer or racemic mixtures thereof. In certain embodiments, provided herein is a method of treating an individual having a disease or disorder, wherein the disease or disorder is caused by, or is associated with, an inappropriate or undesirable immune response, e.g., a disease, disorder or condition that can be treated beneficially by immunosuppression, comprising administering to the individual (S)-3-[4-(4-morphlin-4-ylm-ethylbenzyloxy)-1-oxo-1,3-dihydro-isoindo-2-yl]piperidine-2,6-dione or a pharmaceutically acceptable salt thereof.

In various specific embodiments, said immune-related disease is one or more of selected from Sjögren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroiditis), idiopathic pulmonary fibrosis, idiopathic thrombocytopenia purpura, IgA nephropathy, juvenile arthritis, lichen planus, Ménière disease, mixed connective tissue disease, morephea, narcolepsy, neuromyotonia, pediatric autoimmune neuropsychiatric disorders (PANDAs), pemphigus vulgaris, pernicious anemia, polyarteritis nodosa, polychondritis, polymyalgia rheumatica, primary agammaglobulinemia, primary biliary cirrhosis, Raynaud disease (Raynaud phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, and/or Wegener's granulomatosis.

In certain embodiments, said immune-related disease is asthma, Behcet's disease, chronic inflammatory demyelinating polyneuropathy, and/or idiopathic pulmonary fibrosis.

4.4.4 Treatment for Patients with Renal Impairment

In certain embodiments, provided herein are methods of treating, preventing, and/or managing a disease provided herein in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing a disease provided herein, or a symptom thereof, in patients with impaired renal function comprising administering a therapeutically effective amount of a compound provided herein to the patient with impaired renal function.

In one embodiment, provided herein are methods of preventing a relapse in patients with impaired renal function, comprising administering an effective amount of a compound provided herein to a patient with impaired renal function at risk of having a relapse.

In all of the embodiments provided herein, when a renally impaired patient is treated, there is a need for administering to the renally impaired patient a dose of the compound lower than the dose administered to a normal patient (e.g., a patient without renal impairment) because of the decreased ability of the renally impaired patient in eliminating pomalidomide or its metabolites. Thus, in one embodiment, provided herein is a method for treating a renally impaired patient with a dose of a compound provided herein lower than the dose administered to a normal patient.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day. In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day. In certain embodiments, a therapeutically or prophylactically effective amount of the compound is from about 0.1 to about 100 mg per day, from about 0.5 to about 100 mg per day, from about 1 to about 100 mg per day, from about 0.01 to about 50 mg per day. In certain embodiments, a therapeutically or prophylactically effective amount of the compound is from about 0.1 to about 50 mg per day, from about 0.5 to about 50 mg per day, from about 1 to about 50 mg per day, from about 0.02 to about 25 mg per day, or from about 0.05 to about 10 mg per day.

4.4.5 Treatment for Patients with Cancer

Also provided herein is a method of treating and preventing cancer, which comprises administering to a patient a compound provided herein, e.g., Compound A, or an enantiomer or a mixture of enantiomers thereof, or a pharmaceutically acceptable salt, solvate, hydrate, co-crystal, clathrate, or polymorph thereof.

In another embodiment, provided herein is method of managing cancer, which comprises administering to a patient a compound provided herein, e.g., Compound A, or an enantiomer or a mixture of enantiomers thereof, or a pharmaceutically acceptable salt, solvate, hydrate, co-crystal, clathrate, or polymorph thereof.

Provided herein are methods of treating or managing lymphoma, particularly non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or disorder at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood born tumors. The term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage 1V non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, and/or managing relapsed/refractory multiple myeloma in patients with impaired renal function or a symptom thereof, comprising administering a therapeutically effective amount of Compound A, or an enantiomer or a mixture of enantiomers thereof, or a pharmaceutically acceptable salt, solvate, hydrate, clathrate, stereoisomer, tautomer or racemic mixtures thereof to a patient having relapsed/refractory multiple myeloma with impaired renal function.

In one embodiment, provided herein are methods of preventing relapsed/refractory multiple myeloma in patients with impaired renal function or a symptom thereof, comprising administering an effective amount of Compound A, or an enantiomer or a mixture of enantiomers thereof, or a pharmaceutically acceptable salt, solvate, hydrate, clathrate, stereoisomer, tautomer or racemic mixtures thereof to a patient at risk of having relapsed/refractory multiple myeloma with impaired renal function.

In certain embodiments, provided herein are methods for treating, preventing, and/or managing relapsed/refractory multiple myeloma in patients with impaired renal function. In certain embodiments, provided herein are methods for treating, preventing, and/or managing relapsed/refractory multiple myeloma in patients comprising administering an effective amount of Compound A, or an enantiomer or a mixture of enantiomers thereof, or a pharmaceutically acceptable salt, solvate, hydrate, clathrate, stereoisomer, tautomer or racemic mixtures thereof to a patient.

In certain embodiments, a therapeutically or prophylactically effective amount of the compound A is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount of the compound A is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount of compound A is about 0.1, about 0.2, about 0.3. about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of Compound A, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.01, 0.05, 0.1, 0.2, 0.3, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.01, 0.05, 0.1, 0.2, 0.3, 0.4, 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with NHL (e.g., DLBCL). In a particular embodiment, the compound A can be administered in an amount of about 10 mg/day to patients with NHL (e.g., DLBCL).

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the amount of the compound A administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound A administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, e.g., Compound A, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of Compound A, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has been treated with anticancer therapy prior to the administration of Compound A, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or disorder at issue, as well in one who has not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

Depending on the disease to be treated and the subject's condition, Compound A, or an enantiomer or a mixture of enantiomers thereof; or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound A, or an enantiomer or a mixture of enantiomers thereof; or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, Compound A, or an enantiomer or a mixture of enantiomers thereof; or a pharmaceutically acceptable salt, solvate, hydrate, co-crystal, clathrate, or polymorph thereof, is administered orally. In another embodiment, Compound A, or an enantiomer or a mixture of enantiomers thereof; or a pharmaceutically acceptable salt, solvate, hydrate, co-crystal, clathrate, or polymorph thereof, is administered parenterally. In yet another embodiment, Compound A, or an enantiomer or a mixture of enantiomers thereof; or a pharmaceutically acceptable salt, solvate, hydrate, co-crystal, clathrate, or polymorph thereof, is administered intravenously.

Compound A, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

Compound A, or an enantiomer or a mixture of enantiomers thereof; or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound A, is administered once or more than once each day, for example, for a period of time. The term "continuous" is intended to mean that a therapeutic compound, such as Compound A, is administered daily for an uninterrupted period of at least 10 days to 52 weeks. The term "intermittent" or "intermittently" as used herein is intended to mean stopping and starting at either regular or irregular intervals. For example, intermittent administration of Compound A is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound A, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound A, or an enantiomer or a mixture of enantiomers thereof; or a pharmaceutically acceptable salt, solvate, hydrate, co-crystal, clathrate, or polymorph thereof, is administered once a day. In another embodiment, Compound A, or an enantiomer or a mixture of enantiomers thereof; or a pharmaceutically acceptable salt, solvate, hydrate, co-crystal, clathrate, or polymorph thereof, is administered twice a day. In yet another embodiment, Compound A, or an enantiomer or a mixture of enantiomers thereof; or a pharmaceutically acceptable salt, solvate, hydrate, co-crystal, clathrate, or polymorph thereof, is administered three times a day. In still another embodiment, Compound A, or an enantiomer or a mixture of enantiomers thereof; or a pharmaceutically acceptable salt, solvate, hydrate, co-crystal, clathrate, or polymorph thereof, is administered four times a day.

In certain embodiments, Compound A, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, Compound A, or a pharmaceutically acceptable salt or solvate thereof, is administered once per day for one week, two weeks, three weeks, or four weeks. In one embodiment, Compound A, or an enantiomer or a mixture of enantiomers thereof; or a pharmaceutically acceptable salt, solvate, hydrate, co-crystal, clathrate, or polymorph thereof, is administered once per day for one week. In another embodiment, Compound A, or an enantiomer or a mixture of enantiomers thereof; or a pharmaceutically acceptable salt, solvate, hydrate, co-crystal, clathrate, or polymorph thereof, is administered once per day for two weeks. In yet another embodiment, Compound A, or an enantiomer or a mixture of enantiomers thereof; or a pharmaceutically acceptable salt, solvate, hydrate, co-crystal, clathrate, or polymorph thereof, is administered once per day for three weeks. In still another embodiment, Compound A, or an enantiomer or a mixture of enantiomers thereof; or a pharmaceutically acceptable salt, solvate, hydrate, co-crystal, clathrate, or polymorph thereof, is administered once per day for four weeks.

4.5.5.1 Combination Therapy with a Second Active Agent

Compound A, or an enantiomer or a mixture of enantiomers thereof; or a pharmaceutically acceptable salt, solvate, hydrate, co-crystal, clathrate, or polymorph thereof, can also be combined or used in combination with other therapeutic agents useful in the treatment and/or prevention of cancer described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., Compound A, or an enantiomer or a mixture of enantiomers thereof, or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of Compound A and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of Compound A is independent of the route of administration of a second therapy. In one embodiment, Compound A is administered orally. In another embodiment, Compound A is administered intravenously. Thus, in accordance with these embodiments, Compound A is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, Compound A and a second therapy are administered by the same mode of administration, orally or by IV. In another embodiment, Compound A is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of Compound A provided herein and any optional additional active agents concurrently administered to the patient. In certain embodiments, the second active agent is oblimersen (GENASENSE®), GM-CSF, G-CSF, SCF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with melphalan and dexamethasone to patients with amyloidosis. In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, and steroids can be administered to patients with amyloidosis.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with gemcitabine and cisplatinum to patients with locally advanced or metastatic transitional cell bladder cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with temozolomide to patients with neuroendocrine tumors.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with gemcitabine to patients with recurrent or metastatic head or neck cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with gemcitabine to patients with pancreatic cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with colon cancer in combination with ARISA®, avastatin, taxol, and/or taxotere.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with fluorouracil, leucovorin, and irinotecan to patients with Dukes C & D colorectal cancer or to patients who have been previously treated for metastatic colorectal cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with refractory colorectal cancer in combination with capecitabine, xeloda, and/or CPT-11.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with capecitabine and irinotecan to patients with refractory colorectal cancer or to patients with unresectable or metastatic colorectal carcinoma.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with pegylated interferon alpha to patients with Kaposi's sarcoma.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with fludarabine, carboplatin, and/or topotecan to patients with refractory or relapsed or high-risk acuted myelogenous leukemia.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with liposomal daunorubicin, topotecan and/or cytarabine to patients with unfavorable karotype acute myeloblastic leukemia.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with gemcitabine, abraxane, erlotinib, geftinib, and/or irinotecan to patients with non-small cell lung cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with carboplatin and irinotecan to patients with non-small cell lung cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered with doxetaxol to patients with non-small cell lung cancer who have been previously treated with carbo/VP 16 and radiotherapy.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with carboplatin and/or taxotere, or in combination with carboplatin, paclitaxel and/or thoracic radiotherapy to patients with non-small cell lung cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with taxotere to patients with stage IIIB or IV non-small cell lung cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with oblimersen (Genasense®) to patients with small cell lung cancer.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with ABT-737 (Abbott Laboratories) and/or obatoclax (GX15-070) to patients with lymphoma and other blood cancers.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with taxotere, IL-2, IFN, GM-CSF, PLX4032 (Plexxikon) and/or dacarbazine to patients with various types or stages of melanoma.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered alone or in combination with vinorelbine to patients with malignant mesothelioma, or stage IIIB non-small cell lung cancer with pleural implants or malignant pleural effusion mesothelioma syndrome.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with relapsed or refractory multiple myeloma in combination with doxorubicin (Doxil®), vincristine and/or dexamethasone (Decadron®).

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with various types or stages of gynecologic, uterus or soft tissue sarcoma cancer in combination with IFN, a COX-2 inhibitor such as Celebrex®, and/or sulindac.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) or an enantiomer or a mixture of enantiomers thereof, or a pharmaceutically acceptable salt, solvate, hydrate, co-crystal, clathrate, or polymorph thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, e.g., Compound A, or an enantiomer or a mixture of enantiomers thereof, or a pharmaceutically acceptable salt, solvate, hydrate, co-crystal, clathrate, or polymorph thereof, alleviates or reduces adverse effects which are of such severity that it would otherwise limit the amount of anti-cancer drug.

In one embodiment, a compound provided herein, e.g., Compound A, or an enantiomer or a mixture of enantiomers thereof, or a pharmaceutically acceptable salt, solvate, hydrate, co-crystal, clathrate, or polymorph thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered in combination with specific agents such as heparin, aspirin, coumadin, or G-CSF to avoid adverse effects that are associated with anti-cancer drugs such as but not limited to neutropenia or thrombocytopenia.

In one embodiment, a compound provided herein, e.g., Compound A, or an enantiomer or a mixture of enantiomers thereof, or a pharmaceutically acceptable salt, solvate, hydrate, co-crystal, clathrate, or polymorph thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering Compound A, or an enantiomer or a mixture of enantiomers thereof, or a pharmaceutically acceptable salt, solvate, hydrate, co-crystal, clathrate, or polymorph thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that Compound A may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, e.g., Compound A, or an enantiomer or a mixture of enantiomers thereof, or a pharmaceutically acceptable salt, solvate, hydrate, co-crystal, clathrate, or polymorph thereof, and other active ingredient can be administered to a patient prior to, during, or after the occurrence of the adverse effect associated with conventional therapy.

In one embodiment, Compound A can be administered in an amount ranging from about 0.1 to about 150 mg, from about 1 to about 25 mg, or from about 2 to about 10 mg orally and daily alone, or in combination with a second active agent disclosed herein (see, e.g., section 5.4), prior to, during, or after the use of conventional therapy.

In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, and doxetaxol are administered to patients with non-small cell lung cancer who were previously treated with carbo/VP 16 and radiotherapy.

4.5.5.2 Use with Transplantation Therapy

Compound A, or an enantiomer or a mixture of enantiomers thereof, or a pharmaceutically acceptable salt, solvate, hydrate, co-crystal, clathrate, or polymorph thereof, provided herein can be used to reduce the risk of Graft Versus Host Disease (GVHD). Therefore, encompassed herein is a method of treating, preventing and/or managing cancer, which comprises administering Compound A, or an enantiomer or a mixture of enantiomers thereof, or a pharmaceutically acceptable salt, solvate, hydrate, co-crystal, clathrate, or polymorph thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of Compound A, or an enantiomer or a mixture of enantiomers thereof, or a pharmaceutically acceptable salt, solvate, hydrate, co-crystal, clathrate, or polymorph thereof, provided herein and transplantation therapy provides a unique and unexpected synergism. In particular, Compound A, or an enantiomer or a mixture of enantiomers thereof, or a pharmaceutically acceptable salt, solvate, hydrate, co-crystal, clathrate, or polymorph thereof, exhibits immunomodulatory activity that may provide additive or synergistic effects when given concurrently with transplantation therapy in patients with cancer.

Compound A, or an enantiomer or a mixture of enantiomers thereof, or a pharmaceutically acceptable salt, solvate, hydrate, co-crystal, clathrate, or polymorph thereof, can work in combination with transplantation therapy reducing complications associated with the invasive procedure of transplantation and risk of GVHD. Encompassed herein is a method of treating, preventing and/or managing cancer which comprises administering to a patient (e.g., a human) Compound A, or an enantiomer or a mixture of enantiomers thereof, or a pharmaceutically acceptable salt, solvate, hydrate, co-crystal, clathrate, or polymorph thereof, before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, Compound A, or an enantiomer or a mixture of enantiomers thereof, or a pharmaceutically acceptable salt, solvate, hydrate, co-crystal, clathrate, or polymorph thereof, is administered to patients with multiple myeloma before, during, or after the transplantation of autologous peripheral blood progenitor cell.

In another embodiment, Compound A, or an enantiomer or a mixture of enantiomers thereof, or a pharmaceutically acceptable salt, solvate, hydrate, co-crystal, clathrate, or polymorph thereof, is administered to patients with relapsing multiple myeloma after the stem cell transplantation.

In yet another embodiment, Compound A, or an enantiomer or a mixture of enantiomers thereof, or a pharmaceutically acceptable salt, solvate, hydrate, co-crystal, clathrate, or polymorph thereof, and prednisone are administered as maintenance therapy to patients with multiple myeloma following the transplantation of autologous stem cell.

In yet another embodiment, Compound A, or an enantiomer or a mixture of enantiomers thereof, or a pharmaceutically acceptable salt, solvate, hydrate, co-crystal, clathrate, or polymorph thereof, and dexamethasone are administered as salvage therapy for low risk post transplantation to patients with multiple myeloma.

In yet another embodiment, Compound A, or an enantiomer or a mixture of enantiomers thereof, or a pharmaceutically acceptable salt, solvate, hydrate, co-crystal, clathrate, or polymorph thereof, and dexamethasone are administered as maintenance therapy to patients with multiple myeloma following the transplantation of autologous bone marrow.

In yet another embodiment, Compound A, or an enantiomer or a mixture of enantiomers thereof, or a pharmaceutically acceptable salt, solvate, hydrate, co-crystal, clathrate, or polymorph thereof, is administered following the administration of high dose of melphalan and the transplantation of autologous stem cell to patients with chemotherapy responsive multiple myeloma.

In yet another embodiment, Compound A, or an enantiomer or a mixture of enantiomers thereof, or a pharmaceutically acceptable salt, solvate, hydrate, co-crystal, clathrate, or polymorph thereof, and PEG INTRO-A are administered as maintenance therapy to patients with multiple myeloma following the transplantation of autologous CD34-selected peripheral stem cell.

In yet another embodiment, Compound A, or an enantiomer or a mixture of enantiomers thereof, or a pharmaceutically acceptable salt, solvate, hydrate, co-crystal, clathrate, or polymorph thereof, is administered with post transplant consolidation chemotherapy to patients with newly diagnosed multiple myeloma to evaluate antiangiogenesis.

In still another embodiment, Compound A, or an enantiomer or a mixture of enantiomers thereof, or a pharmaceutically acceptable salt, solvate, hydrate, co-crystal, clathrate, or polymorph thereof, and dexamethasone are administered as maintenance therapy after DCEP consolidation, following the treatment with high dose of melphalan and the transplantation of peripheral blood stem cell to 65 years of age or older patients with multiple myeloma.

In one embodiment, Compound A, or an enantiomer or a mixture of enantiomers thereof, or a pharmaceutically acceptable salt, solvate, hydrate, co-crystal, clathrate, or polymorph thereof, is administered to patients with NHL (e.g., DLBCL) before, during, or after the transplantation of autologous peripheral blood progenitor cell.

In another embodiment, Compound A, or an enantiomer or a mixture of enantiomers thereof, or a pharmaceutically acceptable salt, solvate, hydrate, co-crystal, clathrate, or polymorph thereof, is administered to patients with NHL (e.g., DLBCL) after a stem cell transplantation.

4.5.5.3 Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, Compound A, or an enantiomer or a mixture of enantiomers thereof, or a pharmaceutically acceptable salt, solvate, hydrate, co-crystal, clathrate, or polymorph thereof, provided herein is administered daily in a single or divided doses in a four to six week cycle with a rest period of about a week or two weeks. The cycling method further allows the frequency, number, and length of dosing cycles to be increased. Thus, encompassed herein in certain embodiments is the administration of a compound provided herein, e.g., Compound A, or an enantiomer or a mixture of enantiomers thereof, or a pharmaceutically acceptable salt, solvate, hydrate, co-crystal, clathrate, or polymorph thereof, for more cycles than are typical when it is administered alone. In certain embodiments, a compound provided herein, e.g., Compound A, or an enantiomer or a mixture of enantiomers thereof, or a pharmaceutically acceptable salt, solvate, hydrate, co-crystal, clathrate, or polymorph thereof, is administered for a greater number of cycles that would typically cause dose-limiting toxicity in a patient to whom a second active ingredient is not also being administered.

In one embodiment, Compound A, or an enantiomer or a mixture of enantiomers thereof, or a pharmaceutically acceptable salt, solvate, hydrate, co-crystal, clathrate, or polymorph thereof, is administered daily and continuously for three or four weeks at a dose of from about 0.1 to about 150 mg/d followed by a break of one or two weeks.

In another embodiment, Compound A, or an enantiomer or a mixture of enantiomers thereof, or a pharmaceutically acceptable salt, solvate, hydrate, co-crystal, clathrate, or polymorph thereof, and a second active ingredient are administered orally, with administration of Compound A occurring 30 to 60 minutes prior to a second active ingredient, during a cycle of four to six weeks. In certain embodiments, the combination of Compound A, or an enantiomer or a mixture of enantiomers thereof, or a pharmaceutically acceptable salt, solvate, hydrate, co-crystal, clathrate, or polymorph thereof, and a second active ingredient is administered by intravenous infusion over about 90 minutes every cycle. In certain embodiments, one cycle comprises the administration from about 0.1 to about 150 mg/day of Compound A, or an enantiomer or a mixture of enantiomers thereof, or a pharmaceutically acceptable salt, solvate, hydrate, co-crystal, clathrate, or polymorph thereof, and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

5. EXAMPLES

Embodiments provided herein may be more fully understood by reference to the following examples. These examples are meant to be illustrative of pharmaceutical compositions and dosage forms provided herein, but are not in any way limiting.

5.1 Example 1: Compound A Dosage Capsules

Table 1 illustrates a batch formulation and single dosage formulation for a 0.3 mg strength Compound A single dose unit in a size #4 capsule.

TABLE 1

Formulation for 0.3 mg strength Compound A capsule

| Material | Percent By Weight | Quantity (mg/capsule) |
|---|---|---|
| Compound A | 0.432% | 0.324* |
| Lactose, anhydrous | 74.268% | 55.701 |
| Pregelatinized starch | 25.0% | 18.075 |
| Stearic Acid | 0.300% | 0.225 |
| Total | 100.0% | 75 |

*Denotes amount of the salt form of Compound A that provides the potency of 0.3 mg of the free base of Compound A (i.e., an amount that provides 0.3 mg of 100% pure Compound A).

Compound A was pre-blended with a portion of anhydrous lactose and pregelatinized starch. The pre-blend was passed through a 0.032 inch/20 mesh screen. The remainder of the lactose was milled through a 0.032 inch/20 mesh screen. The pre-blend was blended with the remainder of the lactose. To this blend, stearic acid, which was passed through a 0.0232 inch/30 mesh screen, was further blended. The final blend was encapsulated into a size #4 capsule.

Table 2 illustrates a batch formulation and single dosage formulation for a 0.1 mg strength Compound A single dose unit in a size #4 capsule.

TABLE 2

Formulation for 0.1 mg strength Compound A capsule

| Material | Percent By Weight | Quantity (mg/capsule) |
|---|---|---|
| Compound A | 0.144% | 0.108* |
| Lactose, anhydrous | 74.556% | 55.917 |
| Pregelatinized starch | 25.0% | 18.75 |
| Stearic Acid | 0.300% | 0.225 |
| Total | 100.0% | 75 |

*Denotes amount of the salt form of Compound A that provides the potency of 0.1 mg of the free base of Compound A (i.e., an amount that provides 0.1 mg of 100% pure Compound A).

Compound A was pre-blended with a portion of anhydrous lactose and pregelatinized starch. The pre-blend was passed through a 0.032 inch/20 mesh screen. The remainder of the lactose was milled through a 0.032 inch/20 mesh screen. The pre-blend was blended with the remainder of the lactose. To this blend, stearic acid, which was passed through a 0.0232 inch/30 mesh screen, was further blended. The final blend was encapsulated into a size #4 capsule.

Table 3 illustrates a batch formulation and single dosage formulation for a 0.2 mg strength Compound A single dose unit in a size #3 capsule.

TABLE 3

Formulation for 0.2 mg strength Compound A capsule

| Material | Percent By Weight | Quantity (mg/capsule) |
|---|---|---|
| Compound A | 0.144% | 0.216* |
| Lactose, anhydrous | 74.556% | 111.83 |
| Pregelatinized starch | 25.0% | 37.5 |
| Stearic Acid | 0.300% | 0.45 |
| Total | 100.0% | 150 |

*Denotes amount of the salt form of Compound A that provides the potency of 0.2 mg of the free base of Compound A (i.e., an amount that provides 0.2 mg of 100% pure Compound A).

Compound A was pre-blended with a portion of anhydrous lactose and pregelatinized starch. The pre-blend was passed through a 0.032 inch/20 mesh screen. The remainder of the lactose was milled through a 0.032 inch/20 mesh screen. The pre-blend was blended with the remainder of the lactose. To this blend, stearic acid, which was passed through a 0.0232 inch/30 mesh screen, was further blended. The final blend was encapsulated into a size #3 capsule.

Table 4 illustrates a batch formulation and single dosage formulation for a 0.5 mg strength Compound A single dose unit in a size #3 capsule.

TABLE 4

Formulation for 0.5 mg strength Compound A capsule

| Material | Percent By Weight | Quantity (mg/capsule) |
|---|---|---|
| Compound A | 0.432% | 0.540* |
| Lactose, anhydrous | 74.268% | 92.835 |
| Pregelatinized starch | 25.0% | 31.25 |
| Stearic Acid | 0.300% | 0.375 |
| Total | 100.0% | 125 |

* Denotes amount of the salt form of Compound A that provides the potency of 0.5 mg of the free base of Compound A (i.e., an amount that provides 0.5 mg of 100% pure Compound A).

Compound A was pre-blended with a portion of anhydrous lactose and pregelatinized starch. The pre-blend was passed through a 0.032 inch/20 mesh screen. The remainder of the lactose was milled through a 0.032 inch/20 mesh screen. The pre-blend was blended with the remainder of the lactose. To this blend, stearic acid, which was passed through a 0.0232 inch/30 mesh screen, was further blended. The final blend was encapsulated into a size #3 capsule.

5.2 Example 2: Stability of Formulation

Accelerated stability for 0.3 mg strength PD01-082 formulations (described above in Table 1), as well as other 0.3 mg strength formulations described below in Tables 5-7, was assessed under 40° C./75% RH, and levels of impurities over the time period of initial, 1 month, 3 months, and 6 months were determined. For determination of the level of impurities, an HPLC gradient method was employed using the following conditions:

| Column: | XBridge C18 column, 4.6 × 150 mm, 3.5 µm particle size | | |
|---|---|---|---|
| Temperature: | Autosampler: Ambient; Column: 40° C. | | |
| Mobile Phase: | A: 20 mM Ammonium Acetate: Acetonitrile (95:5, v/v) | | |
| | B: 20 mM Ammonium Acetate: Acetonitrile (10:90, v/v) | | |
| Gradient Profile: | Time (min) | % A | % B |
| | 0 | 100 | 0 |
| | 15 | 0 | 100 |
| | 15.5 | 100 | 0 |
| | 20 | 100 | 0 |
| Flow Rate: | 1.0 mL/min | | |
| Injection Volume: | 50 µL | | |
| Detection: | UV, 240 nm | | |
| Run Time: | 20 minutes. | | |

TABLE 5

Formulation PD01-076 for 0.3 mg strength Compound A capsule

| Material | Percent By Weight | Quantity (mg/capsule) |
|---|---|---|
| Compound A | 0.432% | 0.324* |
| Lactose, anhydrous | 74.268% | 55.701 |
| Microcrystalline cellulose | 25.0% | 18.75 |
| Magnesium stearate | 0.3 | 0.225 |
| Total | 100.0% | 75 |

*Denotes amount of the salt form of Compound A that provides the potency of 0.3 mg of the free base of Compound A (i.e., an amount that provides 0.3 mg of 100% pure Compound A).

TABLE 6

Formulation PD01-078 for 0.3 mg strength Compound A capsule

| Material | Percent By Weight | Quantity (mg/capsule) |
|---|---|---|
| Compound A | 0.432% | 0.324* |
| Lactose, anhydrous | 70.268% | 52.701 |
| Pregelatinized starch | 25.000% | 18.75 |
| Magnesium Stearate | 0.300% | 0.225 |
| Croscarmellose sodium | 4.0% | 3.0 |
| Total | 100.0% | 75 |

*Denotes amount of the salt form of Compound A that provides the potency of 0.3 mg of the free base of Compound A (i.e., an amount that provides 0.3 mg of 100% pure Compound A).

TABLE 7

Formulation PD01-080 for 0.3 mg strength Compound A capsule

| Material | Percent By Weight | Quantity (mg/capsule) |
|---|---|---|
| Compound A | 0.432% | 0.324* |
| Lactose, anhydrous | 70.268% | 52.701 |
| Microcrystalline cellulose | 25.000% | 18.75 |
| Stearic acid | 0.300% | 0.225 |
| Croscarmellose sodium | 4.0% | 3.0 |
| Total | 100.0% | 75 |

*Denotes amount of the salt form of Compound A that provides the potency of 0.3 mg of the free base of Compound A (i.e., an amount that provides 0.3 mg of 100% pure Compound A).

The results are summarized in Tables 8-11 below. From the data shown in Table 8, it was observed that formulation PD01-082 showed least amount of impurities when subjected to 40° C./75% RH. However, gelatin-encapsulated formulations PD01-076, PD01-078 and PD01-080 showed increased total impurity under the same conditions. Furthermore, Table 9 shows a similar stability profile for formulation PD01-082 at 40° C./75% RH when encapsulated in hydroxypropyl methylcellulose (HPMC). The performance characteristics of PD01-082 also maintained throughout the time period investigated. Surprisingly, while all of the formulations tested contained anhydrous or low water content excipients, only formulation PD01-082 exhibited an acceptable stability profile among all the formulations tested. These results show that formulation PD01-082 provided herein has adequate stability for clinical and other uses.

Indeed, the stability of PD0'-082 eliminates the need of storing PD01-082 capsules in desiccant-lined bottles, allowing storage in standard high density polyethylene (HDPE) bottles at significantly less cost. The data presented in Tables 10 and 11 show that desiccant-lined bottles increase the stability of PD0'-076 and PD01-078 to levels comparable to PD01-082 in the less costly HDPE bottles. Although formulations PD01-076 and PD01-078 may be usable in desiccant-lined bottles, the surprising characteristic of formulation PD01-082 eliminates the need for using expensive lined bottles, resulting in substantial cost savings.

TABLE 8

Gelatin capsules in HDPE bottles  
Total impurity at 40° C./75% RH

| | PD01-082 | PD01-076 | PD01-078 | PD01-080 |
|---|---|---|---|---|
| t = 0 | 0.17 | 0.31 | 0.38 | 1.05 |
| t = 1 month | 0.45 | 0.54 | 0.75 | 0.88 |
| t = 2 months | 0.44 | 0.68 | 1.02 | 1.11 |
| t = 3 months | 0.55 | 1.19 | 1.43 | 1.74 |
| t = 6 months | 0.97 | 3.6 | 3.7 | 3.8 |

TABLE 9

HPMC capsules in HDPE bottles  
Total impurity at 40° C./75% RH

| | PD01-082 | PD01-076 | PD01-078 | PD01-080 |
|---|---|---|---|---|
| t = 0 | 0.17 | 0.37 | 0.39 | 0.69 |
| t = 1 month | 0.34 | 1.08 | 0.48 | 0.63 |
| t = 2 months | 0.33 | 2.07 | 0.61 | 0.6 |
| t = 3 months | 0.39 | 3.34 | 0.83 | 0.7 |
| t = 6 months | 0.84 | 8.7 | 2.6 | 2.9 |

TABLE 10

Gelatin capsules in desiccant lined bottles  
Total impurity at 40° C./75% RH

| | PD01-076 | PD01-078 |
|---|---|---|
| t = 0 | 0.31 | 0.38 |
| t = 1 month | 0.45 | 0.51 |
| t = 2 months | 0.38 | 0.46 |
| t = 3 months | 0.32 | 0.28 |
| t = 6 months | 0.37 | 0.41 |

TABLE 11

HPMC capsules in desiccant lined bottles  
Total impurity at 40° C./75% RH

| | PD01-076 | PD01-078 |
|---|---|---|
| t = 0 | 0.37 | 0.39 |
| t = 1 month | 0.36 | 0.52 |
| t = 2 months | 0.33 | 0.5 |
| t = 3 months | 0.36 | 0.27 |
| t = 6 months | 0.44 | 0.39 |

While examples of certain particular embodiments are provided herein, it will be apparent to those skilled in the art that various changes and modifications may be made. Such modifications are also intended to fall within the scope of the appended claims.

What is claimed is:

1. An oral dosage form in the form of a capsule which comprises: 1) Compound A of the following structure:

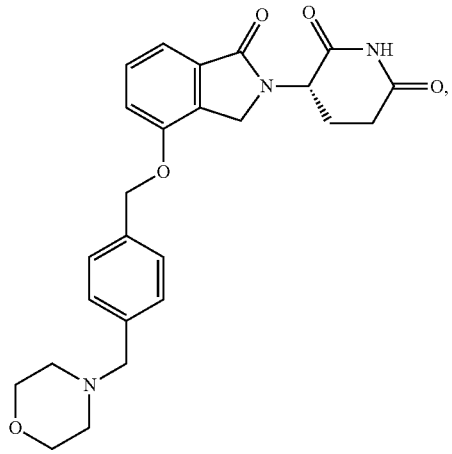 [SMILES: O=C1CC[C@H](N2Cc3c(OCc4ccc(CN5CCOCC5)cc4)cccc3C2=O)C(=O)N1]

or a pharmaceutically acceptable prodrug, salt, solvate, hydrate, clathrate, stereoisomer, tautomer, or racemic mixtures thereof, at an amount of about 0.1 to about 3 weight percent of the total weight of the dosage form; 2) a carrier or excipient at an amount of about 90 to 99.9 weight percent of total weight of the oral dosage form, wherein the carrier or excipient is a mixture of starch and lactose; and 3) a lubricant at an amount of 0.01 to 1 weight percent of total weight of the oral dosage form, wherein the lubricant is stearic acid.

2. The oral dosage form of claim 1, wherein Compound A is present at an amount of about 0.1 to about 1 weight percent of total weight of the dosage form.

3. The oral dosage form of claim 1, wherein the carrier or excipient is present at an amount of about 95 to about 99.9 weight percent of total weight of the dosage form.

4. The oral dosage form of claim 1, wherein the starch is pregelatinized starch.

5. The oral dosage form of claim 1, wherein the lactose is anhydrous lactose.

6. The oral dosage form of claim 1, wherein the lubricant is presented at an amount of 0.1 to 1 weight percent of total weight of the oral dosage form.

7. The oral dosage form of claim 6, wherein the lubricant is present at an amount of 0.1 to 0.5 weight percent of total weight of the dosage form.

8. An oral dosage form which weighs about 75 mg and comprises: 1) Compound A of the following structure:

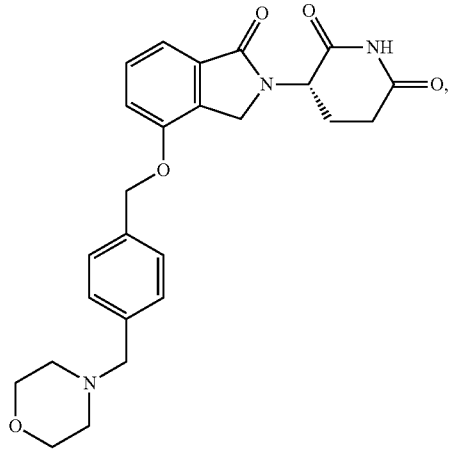 [SMILES: O=C1CC[C@H](N2Cc3c(OCc4ccc(CN5CCOCC5)cc4)cccc3C2=O)C(=O)N1]

or a pharmaceutically acceptable prodrug, salt, solvate, hydrate, clathrate, stereoisomer, tautomer, or racemic mixtures thereof, at an amount that provides 0.3 mg potency of Compound A; 2) a pharmaceutically acceptable carrier or excipient, wherein the carrier or excipient is a mixture of starch and lactose; and 3) a lubricant, wherein the lubricant is stearic acid.

9. The dosage form of claim 8, wherein the starch is pregelatinized starch.

10. The dosage form of claim 9, wherein the pregelatinized starch is present at an amount of about 18.075 mg.

11. The dosage form of claim 8, wherein the stearic acid is present at an amount of about 0.225 mg.

12. The dosage form of claim 8, wherein the lactose is anhydrous lactose.

13. The dosage form of claim 12, wherein the anhydrous lactose is present at an amount that brings the total weight of the composition to about 75 mg.

14. The dosage form of claim 8, which is to be administered in the form of a standard size 4 or larger capsule.

15. An oral dosage form which weighs about 75 mg and comprises: 1) Compound A of the following structure:

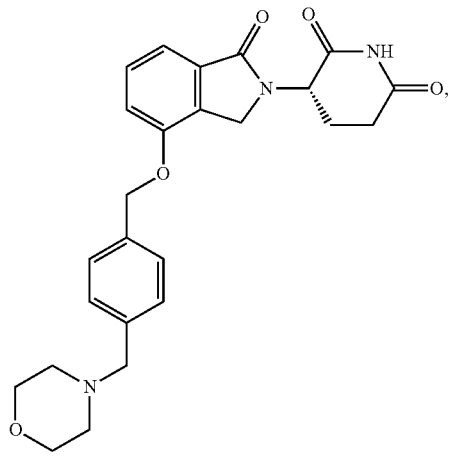 [SMILES: O=C1CC[C@H](N2Cc3c(OCc4ccc(CN5CCOCC5)cc4)cccc3C2=O)C(=O)N1]

or a pharmaceutically acceptable prodrug, salt, solvate, hydrate, clathrate, stereoisomer, tautomer, or racemic mixtures thereof, at an amount that provides 0.1 mg potency of Compound A; 2) a pharmaceutically acceptable carrier or excipient, wherein the carrier or excipient is a mixture of starch and lactose; and 3) a lubricant, wherein the lubricant is stearic acid.

16. The dosage form of claim 15, wherein the starch is pregelatinized starch.

17. The dosage form of claim 16, wherein the pregelatinized starch is present at an amount of about 18.75 mg.

18. The dosage form of claim 15, wherein the stearic acid is present at an amount of about 0.225 mg.

19. The dosage form of claim 15, wherein the lactose is anhydrous lactose.

20. The dosage form of claim 19, wherein the anhydrous lactose is present at an amount that brings the total weight of the composition to about 75 mg.

21. The dosage form of claim 15, which is to be administered in the form of a standard size 4 or larger capsule.

22. An oral dosage form which weighs about 150 mg and comprises: 1) Compound A of the following structure:

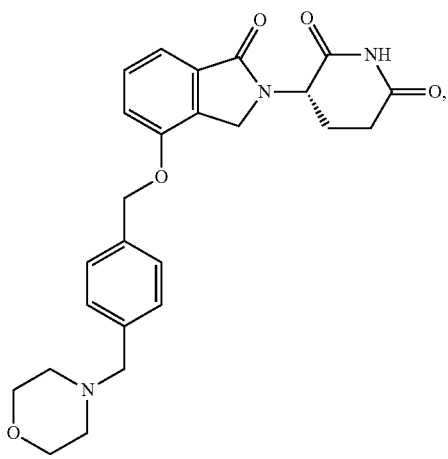 [SMILES: O=C1CC[C@H](N2Cc3c(OCc4ccc(CN5CCOCC5)cc4)cccc3C2=O)C(=O)N1]

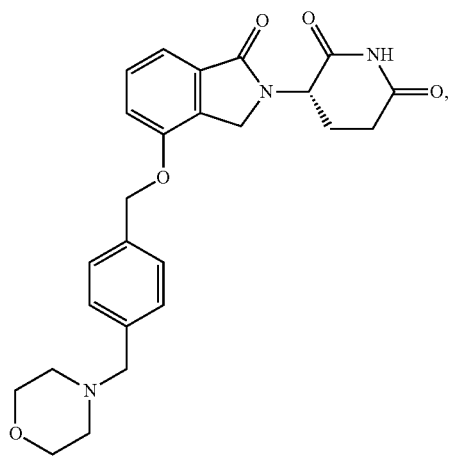 [SMILES: O=C1CC[C@H](N2Cc3c(OCc4ccc(CN5CCOCC5)cc4)cccc3C2=O)C(=O)N1]

or a pharmaceutically acceptable prodrug, salt, solvate, hydrate, clathrate, stereoisomer, tautomer, or racemic mixtures thereof, at an amount that provides 0.2 mg potency of Compound A; 2) a pharmaceutically acceptable carrier or excipient, wherein the carrier or excipient is a mixture of starch and lactose; and 3) a lubricant, wherein the lubricant is stearic acid.

23. The dosage form of claim 22, wherein the starch is pregelatinized starch.

24. The dosage form of claim 23, wherein the pregelatinized starch is present at an amount of about 37.5 mg.

25. The dosage form of claim 22, wherein the stearic acid is present at an amount of about 0.45 mg.

26. The dosage form of claim 22, wherein the lactose is anhydrous lactose.

27. The dosage form of claim 26, wherein the anhydrous lactose is present at an amount that brings the total weight of the composition to about 150 mg.

28. The dosage form of claim 22, which is to be administered in the form of a standard size 3 or larger capsule.

29. An oral dosage form which weighs about 125 mg and comprises: 1) Compound A of the following structure:

or a pharmaceutically acceptable prodrug, salt, solvate, hydrate, clathrate, stereoisomer, tautomer, or racemic mixtures thereof, at an amount that provides 0.5 mg potency of Compound A; 2) a pharmaceutically acceptable carrier or excipient, wherein the carrier or excipient is a mixture of starch and lactose; and 3) a lubricant, wherein the lubricant is stearic acid.

30. The dosage form of claim 29, wherein the starch is pregelatinized starch.

31. The dosage form of claim 30, wherein the pregelatinized starch is present at an amount of about 31.25 mg.

32. The dosage form of claim 29, wherein the stearic acid is present at an amount of about 0.375 mg.

33. The dosage form of claim 29, wherein the lactose is anhydrous lactose.

34. The dosage form of claim 33, wherein the anhydrous lactose is present at an amount that brings the total weight of the composition to about 125 mg.

35. The dosage form of claim 29, which is to be administered in the form of a standard size 3 or larger capsule.

* * * * *

UNITED STATES PATENT AND TRADEMARK OFFICE
CERTIFICATE OF CORRECTION

PATENT NO. : 10,080,801 B2
APPLICATION NO. : 14/508719
DATED : September 25, 2018
INVENTOR(S) : Parikh et al.

It is certified that error appears in the above-identified patent and that said Letters Patent is hereby corrected as shown below:

In the Claims

In Column 51, Line 29 (part of Claim 1), insert the term -- , and wherein the weight ratio of lactose to starch in the oral dosage form is about 3:1 -- after the term "lactose".

In Column 52, Line 5 (part of Claim 8), insert the term -- at an amount of about 90 to 99.9 weight percent of total weight of the oral dosage form -- after the first term "excipient".

In Column 52, Line 6 (part of Claim 8), insert the term -- , and wherein the weight ratio of lactose to starch in the oral dosage form is about 3:1 -- after the term "lactose".

In Column 52, Line 6 (part of Claim 8), insert the term -- at an amount of 0.01 to 1 weight percent of total weight of the oral dosage form -- after the term "lubricant".

In Column 52, Lines 20-21 (part of Claim 14), delete the term "to be administered" after the term "is".

In Column 52, Line 49 (part of Claim 15), insert the term -- at an amount of about 90 to 99.9 weight percent of total weight of the oral dosage form -- after the first term "excipient".

In Column 52, Line 50 (part of Claim 15), insert the term -- , and wherein the weight ratio of lactose to starch in the oral dosage form is about 3:1 -- after the term "lactose".

In Column 52, Line 50 (part of Claim 15), insert the term -- at an amount of 0.01 to 1 weight percent of total weight of the oral dosage form -- after the term "lubricant".

In Column 52, Lines 64-65 (part of Claim 21), delete the term "to be administered" after the term "is".

In Column 53, Line 24 (part of Claim 22), insert the term -- at an amount of about 90 to 99.9 weight percent of total weight of the oral dosage form -- after the first term "excipient".

Signed and Sealed this
Second Day of April, 2019

Andrei Iancu
*Director of the United States Patent and Trademark Office*

CERTIFICATE OF CORRECTION (continued)
U.S. Pat. No. 10,080,801 B2

In Column 53, Line 25 (part of Claim 22), insert the term -- , and wherein the weight ratio of lactose to starch in the oral dosage form is about 3:1 -- after the term "lactose".

In Column 53, Line 25 (part of Claim 22), insert the term -- at an amount of 0.01 to 1 weight percent of total weight of the oral dosage form -- after the term "lubricant".

In Column 53, Lines 38-39 (part of Claim 28), delete the term "to be administered" after the term "is".

In Column 54, Line 25 (part of Claim 29), insert the term -- at an amount of about 90 to 99.9 weight percent of total weight of the oral dosage form -- after the first term "excipient".

In Column 54, Line 26 (part of Claim 29), insert the term -- , and wherein the weight ratio of lactose to starch in the oral dosage form is about 3:1 -- after the term "lactose".

In Column 54, Line 26 (part of Claim 29), insert the term -- at an amount of 0.01 to 1 weight percent of total weight of the oral dosage form -- after the term "lubricant".

In Column 54, Lines 39-40 (part of Claim 35), delete the term "to be administered" after the term "is".